US009144780B2

(12) United States Patent
Taheri et al.

(10) Patent No.: US 9,144,780 B2
(45) Date of Patent: Sep. 29, 2015

(54) PROCESS AND REACTOR FOR DEHYDRATION OF PROPANOL TO PROPYLENE

(71) Applicant: PETRON SCIENTECH INC., Princeton, NJ (US)

(72) Inventors: Hassan Taheri, Hinsdale, IL (US); Yogendra Sarin, Plainsboro, NJ (US); Brian Ozero, Westhampton Beach, NY (US)

(73) Assignee: Petron Scientech, Inc, Princeton, NJ (US)

( * ) Notice: Subject to any disclaimer, the term of this patent is extended or adjusted under 35 U.S.C. 154(b) by 448 days.

(21) Appl. No.: 13/726,935

(22) Filed: Dec. 26, 2012

(65) Prior Publication Data
US 2014/0179972 A1 Jun. 26, 2014

(51) Int. Cl.
| | |
|---|---|
| *B01J 8/02* | (2006.01) |
| *B01J 8/04* | (2006.01) |
| *C07C 1/24* | (2006.01) |
| *B01J 8/00* | (2006.01) |
| *B01J 19/00* | (2006.01) |
| *B01J 19/24* | (2006.01) |
| *B01J 35/00* | (2006.01) |
| *B01J 35/02* | (2006.01) |
| *C07C 1/00* | (2006.01) |
| *C07C 1/20* | (2006.01) |
| *C07C 11/00* | (2006.01) |
| *C07C 11/02* | (2006.01) |
| *C07C 11/06* | (2006.01) |

(52) U.S. Cl.
CPC ............... *B01J 8/0496* (2013.01); *B01J 8/025* (2013.01); *B01J 8/0457* (2013.01); *C07C 1/24* (2013.01); *B01J 8/0453* (2013.01); *B01J 2208/00176* (2013.01); *B01J 2208/00849* (2013.01); *B01J 2208/021* (2013.01); *B01J 2219/0004* (2013.01); *B01J 2219/00038* (2013.01); *C07C 2521/04* (2013.01)

(58) Field of Classification Search
CPC .............. B01J 8/00; B01J 8/02; B01J 8/0242; B01J 8/025; B01J 8/0446–8/0457; B01J 8/0496; B01J 19/00; B01J 19/24; B01J 19/2445; B01J 19/245; B01J 35/00; B01J 35/02; B01J 2208/00–2208/00017; B01J 2208/00106; B01J 2208/00168; B01J 2208/00176; B01J 2208/00849; B01J 2208/02; B01J 2208/021; B01J 2219/00; B01J 2219/00002; B01J 2219/00027; B01J 2219/00038; B01J 2219/0004; C07C 1/20; C07C 1/24; C07C 11/00; C07C 11/02; C07C 11/06; C07C 2521/00; C07C 2521/02; C07C 2521/04; C07C 1/00
See application file for complete search history.

(56) References Cited

U.S. PATENT DOCUMENTS

| | | | | |
|---|---|---|---|---|
| 2,353,509 | A * | 7/1944 | Schulze et al. | 208/74 |
| 4,529,827 | A * | 7/1985 | Drake | 585/640 |
| 4,542,252 | A * | 9/1985 | Graziani et al. | 585/640 |
| 6,734,330 | B1 * | 5/2004 | Xu et al. | 585/640 |

\* cited by examiner

*Primary Examiner* — Natasha Young
(74) *Attorney, Agent, or Firm* — Richard L. Moseley

(57) ABSTRACT

A reactor design and configuration and a process for the catalytic dehydration of propanol to propylene where the reactor train is comprised of a multi-stage single reactor vessel or multiple reactor vessels wherein each stage and/or vessel has different length, internal diameter, and volume than the other stages and/or vessels and in addition the stages and/or reactor vessels are connected in series or in parallel arrangement, preferably used with an improved means of introducing the propanol feedstock and a heat carrying inert gas to the improved reactor train.

4 Claims, 2 Drawing Sheets

ND REACTOR FOR
PROCESS AND REACTOR FOR DEHYDRATION OF PROPANOL TO PROPYLENE

BACKGROUND OF THE INVENTION

1. Field of the Invention

This invention relates to a process for the selective catalytic dehydration of n-propanol or iso-propanol (collectively referred to as propanol) to propylene using an improved technology of reactor design and configuration, wherein the reactor train is comprised of a multi-stage single reactor vessel or multiple reactor vessels wherein each stage and/or vessel has different length, internal diameter, and volume than the other stages and/or vessels and in addition the stages and/or reactor vessels are connected in series or in parallel arrangement. Furthermore, this invention discloses an improved means of introducing the propanol feedstock and a heat carrying inert gas to the improved reactor train.

2. Related Information

Propylene is the second most important raw material in the petrochemicals industry after ethylene. It is the primary feedstock in such diverse materials as polypropylene, propylene oxide, propylene glycol, acrylonitrile, epychlorohydrin, etc. This petrochemical feedstock is primarily produced from petroleum resources by the steam cracking of petroleum-derived feedstocks such as heavy naphtha, ethane/propane, or gas condensates. The economics of these processes are greatly influenced by the supply, availability, and price of crude oil and natural gas. In addition, the cracking processes produce a large number of other valuable products and co-products such as ethylene, butylenes, and other hydrocarbons. which have to be recovered and may not be ignored and disposed of as waste. The economics of the propylene production by the steam cracking process thus requires that these co-products be separated and recovered at very high purity suitable for downstream chemicals and polymer applications. This would require very complex processing scheme, high capital investment, and large energy consumption to separate, purify, and provide storage for all the products so that the process can be economically justified. In addition, the success of the petroleum-derived propylene requires that all the by-products be marketed to their respective end users. If a user of propylene were interested in only producing propylene and no other products, the cracking route is not a viable and profitable option. Furthermore, the conventional steam cracking produces large quantities of $CO_2$ (carbon) which is a main component of the greenhouse gas emission.

The dehydration of propanol is a simple and attractive potential route to propylene. Presently, there is no known commercial process for the catalytic dehydration of propanol. Recently, as the biofuels have attracted more attention globally, as prices of crude oil have increased and have become more unpredictable, and as petroleum supply sources have become more unstable and problematic, the propanol dehydration process is gaining interest as an alternative source for the production of chemical- or polymer-grade propylene. In addition, with the threat to the environment and limited resources in some parts of the world, the propanol dehydration process is being increasingly competitive with the traditional steam cracking process. Furthermore, the sources of raw materials for propanol supply are expanding with a resultant decrease in the cost of propanol manufacture thus making it an attractive option for propylene production.

The propanol dehydration reaction basically is characterized by the removal of a water molecule from propanol and as such is highly endothermic. A significant amount of heat (energy) is thus required to initiate and sustain the reactions to completion. Therefore, the choice of the reactor, its design, and configuration are critical aspects of managing the thermal events within the reactor and controlling the operating temperatures within the catalyst bed for an economical process.

Additionally, the economic production of propylene by this process largely depends on the high conversion of propanol feedstock to avoid recovery and recycle of any unreacted propanol. It also requires high selectivity and yield of the propylene product in order to avoid expensive separation and purification of the final product which is needed for chemicals and polymer applications. Furthermore, it is critical to limit the formation of by-products which will complicate the recovery and purification of the product and its downstream applications into high value added chemicals and polymers.

Unlike the ethanol dehydration process to ethylene which has been the subject of many patents and developments and which has been commercially practiced for many years, there have been very few patents and/or technical articles on the dehydration process of propanol to propylene. Recently, however, there has been some activity with several US patent applications having been filed. US patent application 2009/0259086 discloses an integrated process for the production of mono-olefin(s) from a feedstock comprising of at least one aliphatic paraffinic hydrocarbon. In particular, the disclosure claims a process wherein an alcohol stream containing a mixture of ethanol and propanol is dehydrated within a single reactor to the respective same carbon olefins and other by-products. The olefins thus produced are separated from the other by-products and a mixture of ethylene and propylene is produced as the primary product of the process. The disclosure only provides a general layout of a process for co-dehydrating a mixture of ethanol and propanol with no reference to the choice of the preferred reactor for the optimal temperature control required for the dehydration reactions. Neither does the reference disclose the preferred operating reactions required for an economical process which requires high conversion of the alcohols and high selectivity of the olefins products. The reference claims an operating conversion of ethanol and propanol of preferably between only 20 to 60% per pass, which would require a complex process scheme to recover the valuable alcohols and recycle to the dehydration reaction. Finally, there is not provided in this application any experimental results or evidence to support the claims.

US Patent Application 2009/0270668 discloses an invention for a process to co-produce ethylene and propylene from a mixture of ethanol and propanol feedstock. According to this application, the said feedstock is first processed in a purification column to separate the two alcohols. Following this separation, a parallel path is provided wherein each alcohol is separately dehydrated to its respective olefin. The olefins thus produced are then processed to separate them from the by-products and purified to produce the final ethylene and propylene products. The claimed process is very similar to the above US Patent Application 2009/0259086 with the exception that two dehydration paths are provided in this invention instead of a single integrated dehydration reactor in 2009/0259086 disclosure. Similar to the 2009/0259086, the present invention also does not provide any reference as to the choice of reactors preferred for conducting the endothermic dehydration reactions and the management of the temperatures within the individual reactor vessels. Neither does it provide the preferred operation conditions within the reactor vessels.

US Patent Application 2009/0281362, discloses a process where, unlike the above applications, propanol is the only alcohol feedstock and propylene is the only olefin product. According to this invention, pure propanol is dehydrated in the reactor vessel to propylene and other by-products. The product propylene is then separated from by-products and purified to the final product. There is provided no reference to the preferred choice of the reactor. This invention also does not specify the choice of the reactor and its configuration for optimum performance of the overall process.

In view of the above disclosures, the successful development of technology for propanol dehydration to propylene requires that a reactor design be developed consistent with the thermodynamics and kinetics of the dehydration reactions. Foremost, the reactions in this process are highly endothermic which require input of considerable amount of energy to derive the process. Therefore, supply of heat, the management of the thermal processes, and the reactor temperature control constitute important considerations for optimum performance. One aspect of the present invention is a reactor disclosure to address these issues.

With regard to alcohol dehydration reactors which have been proposed and developed in the past, several patents stand out. U.S. Pat. No. 4,134,926 discloses a fluidized bed reactor concept for the dehydration of ethanol to ethylene wherein a portion of the dehydration catalyst is continuously withdrawn from the reactor chamber and regenerated with air in a second fluid-bed regenerator. The hot regenerated catalyst is then mixed with fresh make-up catalyst and recycled back to the primary reactor to provide the endodermic heat of reaction. This reactor concept has not found commercial application due to the complexity of the process, the handling and recycle of large quantities of solid catalyst, and continuous replacement of the lost catalyst because of attrition.

U.S. Pat. No. 4,232,179 describes a reactor train invention in which multiple, adiabatic reactor vessels are connected in series and/or parallel arrangement for dehydration of ethanol to ethylene. This patent further teaches the use of a sensible heat carrying fluid such as steam mixed with the alcohol feedstock prior to feeding to individual reactors. Each reactor is packed with a solid catalyst. The energy required for the reactions is supplied by a fired heater wherein both alcohol feedstock and steam are heated to very high temperatures needed for the reactions to proceed to completion in each reactor stage. This feature, being similar to British patent 516,360, can also result in lower selectivity and yield of the primary product and the formation of problematic by-products. In addition, no distinction is made in this disclosure as to the relative sizes of each reactor and the catalyst bed within that reactor with respect to other reactors and/or catalyst beds which make up the reactor train.

U.S. Pat. No. 4,396,789 teaches an invention which is basically similar to U.S. Pat. No. 4,232,179 with the exception that the reactor train is designed to operate at a design pressure of between 20 and 40 atmospheres. The patent claims that such high pressure operation will simplify the purification of the crude olefin product during the subsequent cryogenic distillation to produce high quality olefin for downstream chemicals/polymer applications.

In all the above processes, the dehydration catalyst is subjected to carbonization and rapid fouling as a result of direct exposure of the alcohol to the high coil surface temperatures in the fired heater which serves as feed pre-heater. This practice would therefore require frequent regeneration of the catalyst bed thus requiring downtime, loss of production, and shortened catalyst life.

The specific goal of the present invention is to provide a novel, adiabatic reactor configuration and process to achieve the desired goals of the invention. Other objects and benefits of the present invention will become apparent from the following disclosure. Furthermore, it is an object of the present invention to utilize available streams already found within a production facility or derived from the operation of the process carried out in the reactor. In this regard, each of the stages within the reactor vessel is independently sized and the quantity of catalyst therein determined to take advantage of a stream from some other reactor or source within the facility or from other stages within the reactor to obtain the highest yield and selectivity from these disparate sources. It is a particular object of the present invention to design each stage of the reactor considering various sources which can used in the reaction at hand.

SUMMARY OF THE INVENTION

The present invention is an adiabatic gas phase process for catalytic dehydration of propanol to propylene process comprising:

a) feeding propanol through several dehydration stages,
b) the stages are stacked in a series or parallel configuration,
c) each stage has a different internal diameter, length, and volume than the other stages,
d) each stage contains a quantity of fixed bed catalyst whose amount is different than the quantity in other stages within the reactor vessel, and
e) each stage is substantially circular.

A significant aspect of the present invention is an adiabatic gas phase reactor comprising:

a) a plurality of stages, preferably having a substantially circular dimension, such as a cylinder
b) each of said stages having an independently determined internal diameter, length, and volume, and
c) each of said stages contains a quantity of fixed bed catalyst and inert support beds whose amount is independently determined, preferably wherein the independent determinations take into account the control of thermal energy, the optimization of temperature profiles within the catalyst beds, and the feed rates of Propanol and inert gas to the individual stages of the reactor or external to the reactor to obtain the highest efficiency for propanol conversion, propylene selectivity, and yield. The stages can be arranged in series or parallel or in combinations thereof.

The stages, whether housed in a single structure or in separate structures, comprise a reactor train where the dehydration reaction or process is carried out. Each structure is designed to operate under different conditions of temperature, pressure, reactant residence time, and quantity of catalyst than the other structures.

DETAILED DESCRIPTION OF THE INVENTION

Recognizing (i) the short comings of the prior art as noted above, (ii) the key economic drivers needed for bio-propylene production to compete as replacement for petroleum-derived propylene, and (iii) the specific quality demands required of any bio-propylene as feedstock for the downstream chemicals and polymer applications, this invention provides an improved reactor technology and process to specifically address these issues. This disclosure teaches a novel reactor design and geometry and an improved processing concept to achieve its desired goals. The novel reactor is configured according to two embodiments. In each embodiment, the multiple reactor vessels and/or reactor stages are employed in series or in parallel configuration wherein each stage and/or reactor vessel comprising the reactor train has a different internal diameter, length, volume, and quantity of fixed-bed catalyst than the other stages and/or vessels. Several improvements arise from this novel design whose detail is illustrated below. The number of stages is typically between 2 and 10 and preferably between 2 and 5. Each stage preferably has an internal diameter of between 0.5 to 10 meters at the inlet to the stage and an internal diameter of between 0.7 and 15 meters at the outlet of the stage with each stage preferably having a length of between 0.3 to 15 meters.

Figure 1:
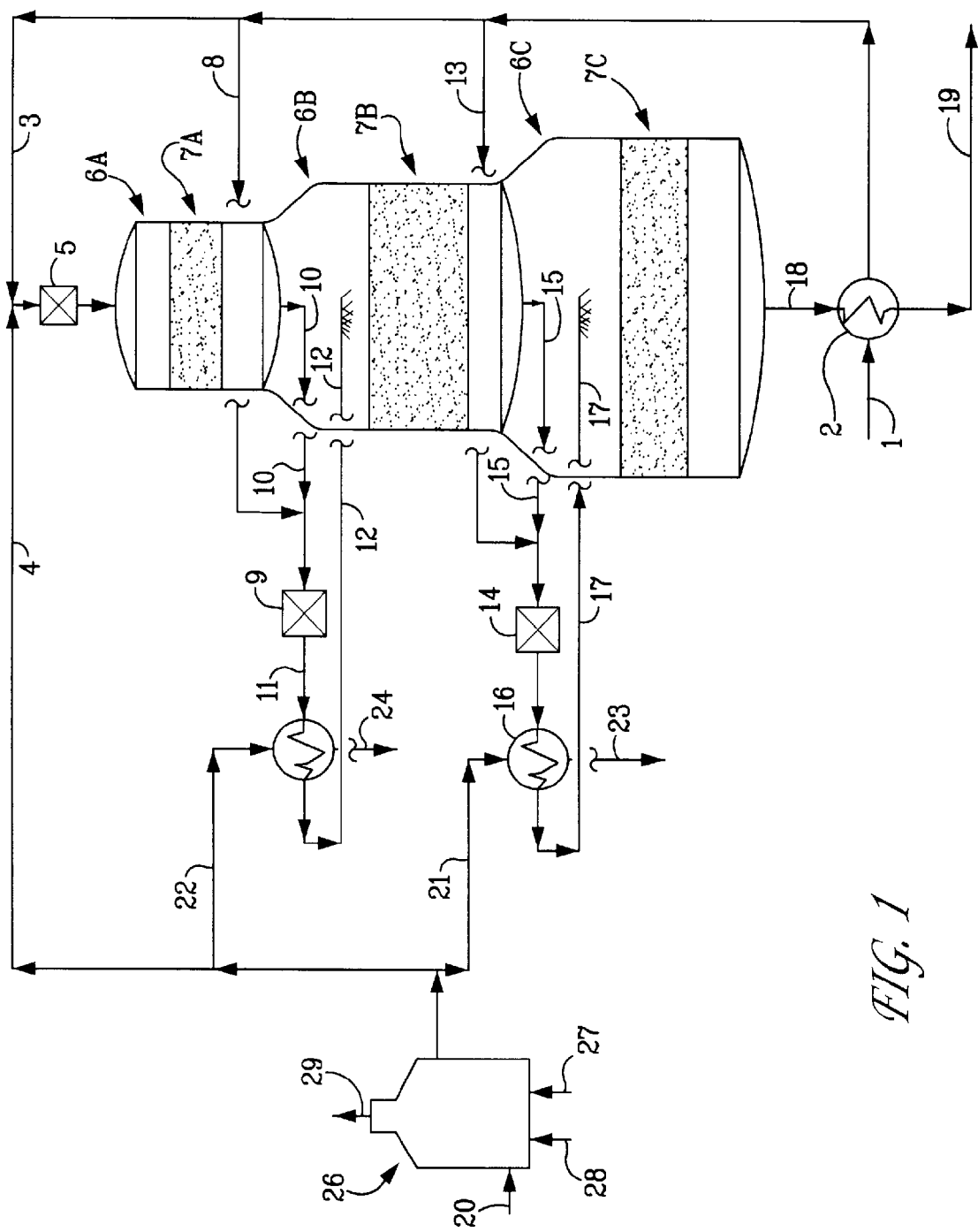
FIG. 1 shows a single reactor vessel housing three catalyst zones in series with each zone having different length, diameter, volume, and/or catalyst quantity than the other zones and the flow arrangement of the reactant alcohol and the inert gas.

According to this disclosure, two embodiments of this process will be described in the following sections. FIG. 1 serves to illustrate one embodiment of this invention. In this particular embodiment, one reactor vessel containing three stages which are connected in series is employed. The three stages comprise the reactor vessel. Each stage is packed with a suitable fixed-bed alcohol dehydration catalyst such as those described in U.S. Pat. Nos. 4,260,845, 4,302,357, 4,529,827, 4,670,620, 4,873,392, and 6,489,515, etc. and US application 2010/0249476. Each stage in this arrangement has a different internal diameter, length, volume, and quantity of catalyst than the other stages. The variable sized stages are uniquely designed for a target production of propylene. The benefits and the improvements made possible by this design will become obvious after the detailed explanation of the invention.

Hydrous or anhydrous propanol stream 1 is first vaporized and preheated in heat exchanger 2 using the hot reactor effluent gases 18 which then exit as stream 19 to downstream purification sections of the plant (not shown). The propanol feed is not passed through a superheating furnace, but is separately pre-heated, to a temperature between 200° to 400° C. and mixed with the heat supplying inert gas in an in-line mixer 5 prior to being introduced into any stage. Propanol is added to each stage at a rate of between 0.01 to 10 kg per hour per kg catalyst and has a weight ratio of between 0.0 to 0.06 and preferably between 0.01 to 0.1 to the weight of the inert gas at the inlet to each stage. Within each stage as optimized according to the present invention, the operating temperature is from 250° C. to 550° C. and preferably from 300° C. to 500° C. at the inlet to each stage and wherein the outlet temperature of each stage is maintained at 200° C. to 500° C. and preferably from 300° C. to 450° C. at operating pressure of each stage is from 2 barg to 50 barg and preferably from 4 barg to 40 barg.

The feed propanol stream 1, after being heated in the exchanger 2, is divided into three streams 3, 8, and 13. Stream 3 is combined with superheated inert gas stream 4 which is supplied by the inert super-heater 26 wherein cold inert gas enters via stream 20 and the heat source is provided by burning fuel supplied by stream 27 and air supplied by stream 28. Alternatively, the superheated inert gas can be supplied via other plant facilities such as a cogeneration plant (not shown). The combustion products from the super-heater 26 leave the stack via stream 29. The inline stationary mixer 5 serves to fully mix the pre-heated propanol stream 3 and superheated stream 4 before entering the first stage reactor 6A. Stage 6A houses the fixed-bed bed catalyst 7A. The diameter, length, and the volume of catalyst in this stage is designed for optimum temperature profile and residence time distribution of the propanol reactant. Typically, the inlet temperature to this stage is between 300 to 550° C. and the outlet in the range of 250 to 480° C. The weight hourly space velocity (WHSV) of propanol in this stage is preferably in the range of 0.01 to 10 kg propanol per hour per kg of catalyst. Typically, the weight ratio of the inert gas to propanol in the inlet to this stage is between 0.1 to 10 kg propanol to one kg of inert gas. The operating pressure in this stage may range from 1 (preferably 2) to 50 barg. These conditions are designed to optimize the temperature profile in this stage and to achieve the complete conversion of propanol and greater than 99% selectivity to the primary product, propylene.

The exit stream 10 from stage 6A containing propylene from stage 1 and water formed in stage 1 is mixed outside of the reactor vessel with fresh propanol stream 8 in inline mixer 9 and heated to the desired temperature by exchanger 11. This exchanger is heated by superheated inert gas stream 22. The heat supplying inert gas to each reactor stage may be superheated steam at pressure in the range of 1 to 50 barg and preferably 4 to 40 barg and at temperature in the range of 300° C. to 550° C. and preferably 350° to 500° C. The inert gas exit from heat exchanger 11 as stream 24 and is used for other heat requirement in the plant. Stream 12 from exchanger 11 is fed to second stage reactor 6B and is distributed downward to the catalyst bed 7B in this stage. The ranges of conditions in this second stage include: inlet temperature of 350-530° C., outlet temperature of 270-460° C., propanol WHSV of 0.01 to 8 kg propanol/hr/kg catalyst, propanol-to-inert gas ratio of 0.8 to 15 kg propanol/kg inert gas and pressure 1 to 50 barg. Again, the conditions are chosen such that to obtain optimum temperature profile thought this second stage catalyst bed, to achieve complete conversion of propanol, and to realize >99% selectivity to propylene.

The effluent stream 15 from second stage reactor is mixed with additional fresh propanol stream 13 in inline mixer 14, heated in exchanger 16. Exchanger 16 is heated by superheated inert gas 21. The heated stream 17 from exchanger 16 is the feed to reactor stage 6C which contains the $3^{rd}$ stage catalyst bed 7C. The operating conditions in this stage are also optimized to achieve similar goals of temperature profile and performance as in stages 6A and 6B. The ranges of conditions in this third stage include: inlet temperature of 340-520° C., outlet temperature of 260-430° C., propanol WHSV of 0.01 to 6 kg propanol/hr/kg catalyst, propanol-to-inert gas ratio of 1 to 20 kg propanol/kg inert gas, and pressure in the range 1 to 50 barg. The exit stream 18 from stage 6C flows to heat exchanger 18. Stream 19 containing crude propylene product, inert gas, the water formed in alcohol dehydration, and minor by-products exits this exchanger and is processed in downstream equipment for separation and purification or propylene.

Figure 2:
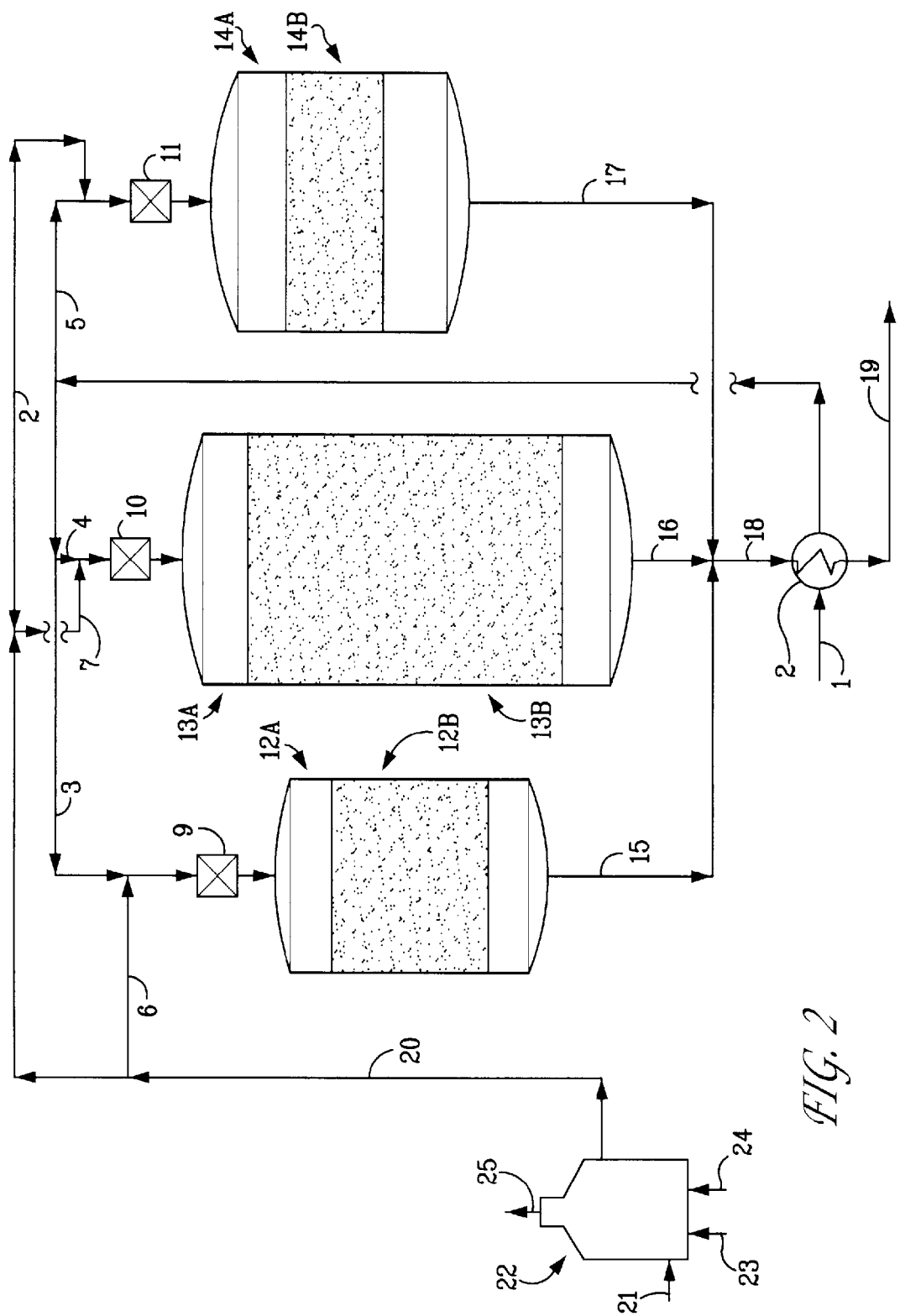
FIG. 2 depicts a second embodiment of the invention where three reactor vessels which are arranged in series to comprise the reactor train with each vessel in this embodiment having different length, diameter, volume, and/or catalyst quantity than the other vessels.

A second embodiment of the present invention is illustrated in FIG. 2. In this illustration, three reactor vessels are shown in parallel. The distinction between this variation and the variation shown in FIG. 1 is that, unlike the single reactor vessel with multiple catalyst stages and with each stage having different volume as shown in FIG. 1, there is one catalyst stage in each of the reactor vessels in the present variation. The reactor vessels are designed such that to utilize the available streams effectively and result in optimum distribution of alcohol into each reactor vessel. Similar to the previous variation, each vessel in this arrangement has a different internal diameter, length, and volume than the other reactor vessels. In addition, the quantity of catalyst in each vessel is different than the quantity in other reactor vessels.

As FIG. 2 illustrates, the fresh propanol stream 1 is vaporized and pre-heated in heat exchanger 2 prior to being divided into three streams 3, 4, and 5. Stream 3 is mixed with superheated inert gas stream 6 in inline mixer 9 and fed to the first reactor vessel 12A which contains the catalyst bed 12B. In similar fashion, stream 4 is mixed with superheated inert gas stream 7 in mixer 10 and fed to the second reactor vessel 13A which houses the catalyst bed 13B. Still in similar fashion, fresh propanol stream 5 is mixed with superheated inert gas stream 8 in inline mixer 11. The mixture is fed to reactor vessel 14A which holds the catalyst bed 14B. The exits streams 15 from reactor vessel 12, exit stream 16 from reactor vessel 13A, and exit stream 17 from reactor vessel 14A are combined and heat exchanged in exchanger 18 before taken to propylene recovery and purification sections of the plant (not shown).

The operating conditions within the individual reactor vessels in this arrangement are such, to achieve the desired performance criteria of optimum temperature profiles within the individual catalyst beds, complete conversion of propanol feedstock, and >99% selectivity to propylene product. The ranges for these conditions include the following. Typically, the inlet temperature to each reactor vessel is between 350 to 550° C. and the outlet in the range of 270 to 480° C. The weight hourly space velocity (WHSV) of the propanol in each vessel is in the range of 0.01 to 10 kg propanol per hour per kg of catalyst. The weight ratio of the inert gas to propanol in the inlet to this stage is between 0.5 to 10 kg propanol to inert gas. Finally, the operating pressure within each reactor vessel may range from 1 to 50 barg.

To those skilled in the art, the design features as detailed in above paragraphs and the accompanying figures offer major technical advances and make it possible to realize numerous improvements and advantages over the previous arts. These advances and improvements are noted in the following paragraphs.

As explained before, the catalytic dehydration of propanol to propylene is highly endothermic and requires considerable supply of energy to initiate the reaction and drive it to completion. The reaction produces one mole of water for each mole of propanol reacted according to:

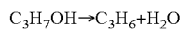

$$C_3H_7OH \rightarrow C_3H_6 + H_2O$$

This reaction requires about 300 kcal per kg of propylene at the normal operating temperatures of 300°-400° C.

Competing reactions may also take place producing the undesirable by-product such as ether.

The key is to minimize the formation of the by-products and maximize the selectivity to propylene product by the optimum arrangement and size of the reactor stages and the staged addition of propanol and the heat supplying inert gas. A further consideration is to limit the secondary reaction of propylene to other hydrocarbons which results in lower selectivity and yield.

The kinetics of the primary reaction are very sensitive to the operating temperature regime within the catalyst bed. At the inlet to the reactor, the temperature has to be high enough to initiate the reactions. If the temperature of the gas mixture is too high at the inlet region to the catalyst, degradation and side reactions of propanol will occur resulting in unwanted products. This reduces selectivity and yield to the desired propylene product. As reactants pass through each catalyst bed, the temperature is continuously decreased toward the end of the catalyst bed due to the endothermicity of the reactions. At the outlet of the catalyst bed, if the temperature is allowed to cool significantly because of inadequate supply of sensible energy, either propanol conversion is not complete thus requiring recycle of propanol or secondary reactions can occur resulting in unwanted by-products such as aldehydes and ethers. Therefore, the temperature profile through the catalyst bed is very critical to optimum performance.

Three design features in this invention combine to result in optimum temperature profile within the individual reactors. First, the multiple staging of the reactors into variable volume compartments allows for the optimum distribution and residence time of the reactant alcohol and inert gas through each stage. The variable volume is achieved by varying the internal diameter of each reactor stage, varying the length of each stage, and/or varying the volume of the catalyst bed within each stage. Stages may have continuously variable internal diameter from the inlet of the stage to the outlet of the stage. The optimization of volume and thus the residence time distribution of the reactants is an important consideration in the kinetics of the dehydration reaction and therefore the optimum full and even utilization of the individual catalyst beds within the reactor stages.

Second, both the propanol feed and the heat supplying inert gas to each stage are separately and independently fed, controlled, and heated prior to being mixed and distributed to the individual reactor stages. This makes it possible to avoid super-heating of propanol and its thermal degradation and coke formation. In addition, this feature allows the optimum utilization of the heat carrying inert gas in relation to the amount of propanol feed rate. This optimization requires the balancing of sufficient energy supply to each stage but not excessive amounts which will result in economic disadvantage. The design also balances the formation of the water of reaction and the heat supplying inert gas. Furthermore, the design eliminates the formation of by-products such as ether, aldehydes, or hydrocarbons.

The third design improvement embodied in this invention stems from the kinetics of the dehydration reaction and is based on arranging the catalyst stages and selecting the operating conditions in each stage in order to make it possible for the complete conversion of propanol through the individual reactor stages. Therefore, the costly propanol recovery and recycle are avoided in this processing scheme.

A further improvement of the present invention is that the economic life of each catalyst bed comprising the reactor train is considerably increased due to the optimum temperature profile within each stage. Therefore, frequent regenerations required in older technologies are avoided. The catalyst employed in this process may be alumina, silica-alumina, zeolites, or other suitable catalysts as are described in the patent literature. See for example U.S. Pat. Nos. 4,260,845, 4,302,357, 4,529,827, 4,670,620, 4,873,392, and 6,489,515, and US patent application 2010/0249476. The longer catalyst life makes it possible for improved asset utilization and efficiency and allows for longer cycle time of the catalyst beds before unit shutdown and catalyst replacement are needed.

A further improvement resulting from the reactor design and the staged process for introducing propanol feed and the heat supplying inert gas into each stage and/or reactor vessel is that each stage may be by-passed to control the production rate or make it possible to perform maintenance in that stage without losing efficiency or shutting down the whole process. Furthermore, this allows for partial or total removal of the catalyst bed in a particular stage without having to shut down the whole process.

In addition to the above improvements, other improvements can be readily realized from this invention by those experts familiar with the selective dehydration of propanol to propylene.

Examples

The following experimental examples serve to illustrate the unique features of the present invention and the resulting performance of the dehydration system. An experimental pilot reactor was constructed to allow the simulation of the operating conditions within each reactor stage and the performance testing of the reactor design as taught in this invention. The reactor consisted of a 1 inch OD, 0.870 inch ID, 3.5 feet long fix-bed down flow reactor. The reactor was heated in a three-zone furnace whereby the temperature of each zone could be controlled independently to achieve a desired temperature profile within the catalyst bed. The reactor tube was equipped with a centrally positioned 3/16" thermowell which housed five stationary thermocouples that were equally spaced within the thermowell at 0", 2", 4", 6", and 8" measured from the top of the catalyst bed.

The catalyst used in these experiments was a commercially available high purity and surface area gamma alumina. Approximately 40 CC of this catalyst was loaded into the reactor. An equal volume of inert alpha alumina spheres was mixed with the active catalyst as diluent yielding a total bed volume of ~80 CC. In addition, the same inert alumina spheres were used as pre- and post-heat zones of the reactor. The complete inertness of the spheres was demonstrated under all the operating conditions by testing the pilot reactor with only the alpha alumina packed inside the reactor tube.

The experimental setup was designed for continuous operation, sampling, and analysis of the products. The operating conditions were selected such that to simulate the ranges of the operating conditions within a two-stage design. The experimental conditions were as shown in Table 1:

TABLE 1

Experimental Conditions

| | |
|---|---|
| Pressure, barg | 6.45 |
| Inlet Temperature, ° C. | 466 |
| Outlet Temperature, ° C. | 375 |
| Feed Propanol Conc., mole % | 8.75 |
| Feed Water Conc., mole % | 91.25 |
| Propanol WHSV, g/hr/g cat. | 0.433 |

The performance measures in these tests included the determination of propanol conversion, the selectivity to propylene, and the extent of by-products formation. The by-products which were analyzed included methane, ethane, propylene, propane, methanol, ethanol, propanol, acetaldehyde, 1-butane, 2-butane, acetone, diethyl ether, n-pentane, 1-pentene, 1-hexene, n-hexane, n-butanol. The test results are summarized in Table 2.

Propanol conversion was determined by

% Conversion=(propanol in−propanol out)×100/(propanol in)

Propylene selectivity was determined by:

Selectivity=propylene formed×100/total products formed

TABLE 2

Performance Data

| | |
|---|---|
| Propanol Conversion, % | 100 |
| Propylene Selectivity, % | 100 |
| By-products Conc., % | -ND |

ND: Not Detected

The invention claimed is:

1. An adiabatic reactor train configuration for application to the catalytic dehydration of propanol to propylene process wherein:
   a) the train is comprised of several adiabatic gas phase reactor stages,
   b) the reactor stages are connected in a series or parallel configuration,
   c) each reactor stage has a different internal diameter, length, and volume than the other stages,
   d) each reactor stage contains a quantity of fixed bed catalyst whose amount is different that the quantity in other stages, and
   e) each stage is substantially circular.

2. The reactor train according to claim 1 wherein each stage has continuously variable internal diameter from the inlet of the stage to the outlet of the stage.

3. The reactor train according to claim 1 wherein:
   the number of reactor stages is between 2 and 10 and preferably between 2 and 5, each reactor stage has an internal diameter of between 0.5 to 10 meters at the inlet to the stage and an internal diameter of between 0.7 and 15 meters at the outlet of the stage, and each stage has a length of between 0.3 to 15 meters.

4. An adiabatic train process for the catalytic dehydration of propanol to propylene process wherein:
   a) the train process is comprised of feeding propanol through several adiabatic gas phase dehydration reactor stages,
   b) the reactor stages are connected in a series or parallel configuration,
   c) each reactor stage has a different internal diameter, length, and volume than the other stages,
   d) each reactor stage contains a quantity of fixed bed catalyst whose amount is different that the quantity in other stages, and
   e) each stage is substantially circular.

* * * * *